(12) United States Patent
De Luca et al.

(10) Patent No.: US 9,406,212 B2
(45) Date of Patent: *Aug. 2, 2016

(54) AUTOMATED MONITORING AND CONTROL OF CONTAMINATION ACTIVITY IN A PRODUCTION AREA

(75) Inventors: Nicholas De Luca, San Juan, PR (US); Koichi Sato, Saratoga, CA (US)

(73) Assignee: Sealed Air Corporation (US), Elmwood Park, NJ (US)

( * ) Notice: Subject to any disclaimer, the term of this patent is extended or adjusted under 35 U.S.C. 154(b) by 1157 days.

This patent is subject to a terminal disclaimer.

(21) Appl. No.: 12/931,294

(22) Filed: Jan. 28, 2011

(65) Prior Publication Data

US 2012/0150333 A1 Jun. 14, 2012

Related U.S. Application Data

(63) Continuation-in-part of application No. 12/928,362, filed on Dec. 9, 2010, now Pat. No. 9,189,949.

(60) Provisional application No. 61/341,655, filed on Apr. 1, 2010.

(51) Int. Cl.
*G08B 13/14* (2006.01)
*G08B 23/00* (2006.01)
(Continued)

(52) U.S. Cl.
CPC ............ *G08B 21/12* (2013.01); *G06K 9/00771* (2013.01); *G06Q 10/08* (2013.01); *G08B 13/1427* (2013.01); *G08B 21/22* (2013.01); *G08B 21/245* (2013.01); *G06F 19/327* (2013.01)

(58) Field of Classification Search
CPC .... G08B 13/1427; G08B 21/22; G08B 21/12; G08B 21/24; G08B 3/10; G06K 9/00281; G06Q 10/08
USPC .................. 340/568.1, 10.1, 500, 540, 573.1, 340/686.1, 686.2, 686.6; 382/103, 115, 382/100, 182, 286, 291; 348/143, 77, 94
See application file for complete search history.

(56) References Cited

U.S. PATENT DOCUMENTS 5,023,597 A 6/1991 Salisbury
5,164,707 A * 11/1992 Rasmussen et al. .......... 340/551
(Continued)

FOREIGN PATENT DOCUMENTS

EP 1 939 811 A1 7/2008
KR 100 789 721 B1 2/2007
(Continued)

OTHER PUBLICATIONS

Hydra: Multiple People detection and Tracking Using Silhouettes, Haritaoglu et al, Computer Vision Laboratory, University of MD, 8 pages (1999).
(Continued)

*Primary Examiner* — Hoi Lau
(74) *Attorney, Agent, or Firm* — Capitol City TechLaw; Jasbir Singh

(57) ABSTRACT

An automated process for monitoring and controlling contamination activity in a production area comprises capturing image from the production area over a period of time, processing the image data with a computer to determine whether a contamination event has occurred in the production area, and activating a contamination control device in accordance with the processing of the image data. The contamination event can be a germ-releasing event from an individual in the production area, a pipe leaking fluid into the production area, etc. The automated monitoring and control may also determine whether an article of contamination control equipment (e.g., face mask, glove, etc) is properly positioned on the individual to prevent the contamination from entering the production area in a form that could contaminate product, equipment, or the production area itself. An automated system for monitoring and controlling contamination includes a computer, an imaging sensor in communication with the computer, and a computer-readable program code disposed on the computer.

28 Claims, 6 Drawing Sheets

(51) Int. Cl.

| | |
|---|---|
| G08B 21/00 | (2006.01) |
| G08B 21/12 | (2006.01) |
| G08B 21/24 | (2006.01) |
| G08B 21/22 | (2006.01) |
| G06Q 10/08 | (2012.01) |
| G06K 9/00 | (2006.01) |
| G06F 19/00 | (2011.01) |

(56) References Cited

U.S. PATENT DOCUMENTS

| | | | |
|---|---|---|---|
| 5,305,390 | A | 4/1994 | Frey et al. |
| 5,465,115 | A | 11/1995 | Conrad et al. |
| 5,781,650 | A | 7/1998 | Lobo et al. |
| 5,973,732 | A | 10/1999 | Guthrie |
| 6,104,966 | A | 8/2000 | Haagensen |
| 6,166,729 | A | 12/2000 | Acosta et al. |
| 6,208,260 | B1 | 3/2001 | West et al. |
| 6,283,860 | B1 | 9/2001 | Lyons et al. |
| 6,392,546 | B1 | 5/2002 | Smith |
| 6,600,475 | B2 | 7/2003 | Gutta et al. |
| 6,650,242 | B2 | 11/2003 | Clerk et al. |
| 6,697,104 | B1 | 2/2004 | Yakobi et al. |
| 6,761,447 | B1* | 7/2004 | Pyo ............................... 351/41 |
| 6,853,303 | B2 | 2/2005 | Chen et al. |
| 6,970,574 | B1 | 11/2005 | Johnson |
| 7,015,816 | B2 | 3/2006 | Wildman et al. |
| 7,065,645 | B2 | 6/2006 | Teicher |
| 7,149,598 | B1* | 12/2006 | Yao ............................... 700/121 |
| 7,317,830 | B1* | 1/2008 | Gordon et al. ................ 382/173 |
| 7,319,399 | B2 | 1/2008 | Berg |
| 7,375,640 | B1 | 5/2008 | Plost |
| 7,464,001 | B1 | 12/2008 | Adams |
| 7,495,569 | B2 | 2/2009 | Pittz |
| 7,689,465 | B1 | 3/2010 | Shakes et al. |
| 7,832,396 | B2 | 11/2010 | Abernethy |
| 8,208,681 | B2 | 6/2012 | Heller et al. |
| 8,279,277 | B2 | 10/2012 | Nam et al. |
| 2002/0190866 | A1* | 12/2002 | Richardson .................. 340/632 |
| 2003/0058111 | A1 | 3/2003 | Lee et al. |
| 2003/0061005 | A1 | 3/2003 | Manegold et al. |
| 2003/0093200 | A1 | 5/2003 | Gutta et al. |
| 2003/0169906 | A1 | 9/2003 | Gokturk et al. |
| 2005/0027618 | A1 | 2/2005 | Zucker et al. |
| 2005/0094879 | A1 | 5/2005 | Harville |
| 2005/0248461 | A1 | 11/2005 | Lane et al. |
| 2006/0033625 | A1 | 2/2006 | Johnson et al. |
| 2006/0219961 | A1 | 10/2006 | Ross et al. |
| 2006/0220787 | A1 | 10/2006 | Turner et al. |
| 2006/0272361 | A1 | 12/2006 | Snodgrass |
| 2008/0001763 | A1 | 1/2008 | Raja et al. |
| 2008/0031838 | A1 | 2/2008 | Bolling |
| 2008/0136649 | A1 | 6/2008 | Van De Hey |
| 2008/0171501 | A1* | 7/2008 | Woods et al. ................ 451/451 |
| 2008/0189142 | A1 | 8/2008 | Brown et al. |
| 2008/0247609 | A1* | 10/2008 | Feris et al. ................... 382/118 |
| 2009/0040014 | A1 | 2/2009 | Knopf et al. |
| 2009/0051545 | A1 | 2/2009 | Koblasz |
| 2009/0079822 | A1 | 3/2009 | Yoo et al. |
| 2009/0128311 | A1 | 5/2009 | Nishimura et al. |
| 2009/0135009 | A1 | 5/2009 | Little et al. |
| 2009/0161918 | A1* | 6/2009 | Heller et al. ................. 382/115 |
| 2009/0195382 | A1 | 8/2009 | Hall |
| 2009/0224868 | A1 | 9/2009 | Liu et al. |
| 2009/0224924 | A1 | 9/2009 | Thorp |
| 2009/0237499 | A1 | 9/2009 | Kressel et al. |
| 2009/0271243 | A1* | 10/2009 | Sholl et al. .................... 705/9 |
| 2009/0273477 | A1 | 11/2009 | Barnhill |
| 2010/0155416 | A1 | 6/2010 | Johnson |
| 2010/0167248 | A1 | 7/2010 | Ryan |
| 2010/0183218 | A1 | 7/2010 | Naito et al. |
| 2010/0245554 | A1* | 9/2010 | Nam et al. .................... 348/77 |
| 2012/0062725 | A1 | 3/2012 | Wampler et al. |
| 2012/0146789 | A1 | 6/2012 | De Luca et al. |

FOREIGN PATENT DOCUMENTS

| | | |
|---|---|---|
| WO | 99/32959 | 7/1999 |
| WO | 2007/090470 | 8/2007 |
| WO | 2007/129289 A1 | 11/2007 |
| WO | 2008/152433 A1 | 12/2008 |
| WO | 2010/026581 A2 | 11/2010 |

OTHER PUBLICATIONS

Face and Hand Gesture Recognition Using Hybrid Classifiers, Gutta et al, Dept. of Computer Science, George Mason University, 6 pages (1996).

Maximum Likelihood Face Detection, Colmenarez et al, University of ILL, 4 pages, (1996).

Video Sequence Interpretation for Visual Surveillance, Rota et al, pp. 1-9 (2000).

Lyons, D.C., et al, "A Line-Scan Computer Vision Algorithm for Identifying Human Body Features", International Gesture Workshop, GW '99, Gif-Sur-Yvette, France, Mar. 17-19, 1999, pp. 85-96.

Application of the Self-Organizing Map to Trajectory Classification, Owens et al, School of Computing and Engineering Technology, University of Sunderland, pp. 1-7 (2000).

Detecting Human Faces in Color Images, Yang et al, Beckman Institute and Department of Electrical and Computer Engineering, University of ILL, pp. 127-130, (1998).

A. Criminisi, A. Zisserman, L. Van Gool, Bramble S., and D. Compton, "A New Approach to Obtain Height Measurements from Video", Proc. of SPIE, Boston, Massachussets, USA, vol. 3576, pp. 227-238 (Nov. 1-6, 1998).

A Revolution in Traceability, FOODproductiondaily.com, 3 pages, (Mar. 10, 2004).

Eye in the Sky (camera), Wikipedia, 1 page (Dec. 11, 2009).

Edge Detection, Wikipedia, 8 pages. (Feb. 10, 2010).

Corner Detection, Wikipedia, 12 pages (Feb. 9, 2010).

Athanasia et al, "P1714 Compliance of healthcare workers with hand hygiene rules in the emergency room of two tertiary hospitals in the area of Athens", International Journal of Antimicrobial Agents, Elsevier Science, Amsterdam, NL, vol. 29, Mar. 1, 2007, p. S486, SP022038903, ISSN: 0924-8579, DOI:DOI:10.1016/S0924-8579(07)71553-4.

Chapter 17: "Beyond one Still Image: Face Recognition from Multiple Still Images or a Video Sequence"; In: Shao, Wenyi (Ed.); Chellappa, Rama (Ed.): "Face Processing—Advanced Modeling and Methods", Academic Press/Elsevier, US, UK 313230, XP002639937, ISBN: 978-0-12-088452-0, pp. 547-575.

Grange, Sebastian, Baur, charles: Robust Real-time 3D Detection of Obstructed Head and Hands in Indoors Environments:, J. Multimedia, vol. 1, No. 4, Jul. 2006, pp. 29-36, XP002639938, US.

United States Department of Agriculture: "Machine Vision sees food contamination we can't see", Agricultural Research Magazine, vol. 50, No. Aug. 8, 2002, XP8137410, US, retrieved from the internet: URL:http://www.ars.usda.gov/is/AR/archive/aug02/food0802.pdf {retrieved on May 31, 2011].

Bhatt J et al: "Automatic recognition of a baby gesture", Proceedings 15th IEEE International Conference on Tools with Artificial Intelligence. ICTAI 2003. Sacramento, CA, Nov. 3-5, 2003; Los Alamitos, CA, IEEE Comp. Soc, US, vol. Conf. 15, Nov. 3, 2003, pp. 1-6, XP010672284, DOI: DOI:10.1109/TAI.2003.1250248 ISBN: 978-0/7695-2038-4.

Lohr, S., "Computers That See You and Keep Watch Over You," The New York Times, 5 pages, Jan. 1, 2011.

"GE Healthcare's Smart Patient Room to Begin data Collection," 3 pages, Sep. 15, 2010.

* cited by examiner

AUTOMATED MONITORING AND CONTROL OF CONTAMINATION ACTIVITY IN A PRODUCTION AREA

REFERENCE TO RELATED APPLICATIONS

This application is a continuation-in-part of U.S. Ser. No. 12/928,362, filed 9 Dec. 2010 now U.S. Pat. No. 9,189,949, in the name of De Luca et al, entitled "Automated Monitoring and Control of Contamination in a Production Area", which is hereby incorporated, in its entirety, by reference thereto. This application also claims priority from provisional U.S. Ser. No. 61/341,655, filed 1 Apr. 2010, also in the name of De Luca et al, also entitled "Automated Monitoring and Control of Contamination in a Production Area", which is also hereby incorporated, in its entirety, by reference thereto.

BACKGROUND

The invention is directed to the automated monitoring and control of a wide variety of forms of contamination in a production area. As individuals can be a primary source of contamination, the invention is also directed to the automated monitoring and control of contamination of the production area by an individuals working in the production area.

While contamination of a production area can occur by a leaking pipe, a machine that breaks and sends a fragment into the production area and possibly into a product or other production machine, smoke or other atmospheric particulates entering the atmosphere of the production area from outside the production area, it is contamination by actions of workers in a production area are the most likely source of a variety of contaminants being released into a production area. Contamination of a production area can occur if an individual in a production area spills a material, breaks an object, touches an object, or simply coughs or sneezes in the production area. Other contaminating activities include sweating, excreting, bleeding, belching, crying, or vomiting in the production area.

Contamination of a production area, particularly contamination of product being produced in a production area, occurs in a wide variety of industries, and has a detrimental impact in production areas in which hygiene is needed to prevent contamination by biological and other contaminants. Such industries include the food industry, the pharmaceutical industry, and other health-services and health-product related industries, in which microbial and other contamination can have adverse consequences on the consumer of the services and/or products. The presence of bacteria, phlegm, saliva, sweat, skin oils, airborne microbes, and other contaminants from workers can result in product defects and spread of disease during one or more phases of a manufacturing process or during one or more phases of a process of rendering services.

Other industries require contamination-free, high purity production environments because contamination can negatively impact the function and/or aesthetics of the resulting product. One such industry is the manufacture of semiconductor devices, microelectronics, microchips, and integrated circuits. Another industry in which contamination negatively impacts product quality is the coating (e.g., painting) of various products, including automotive, furniture, construction, and other products, in which contaminants adversely affect the appearance, feel, or durability of the coating applied to the product.

Although there are numerous vendors supplying the market with contamination control equipment (hereinafter, "CCE") intended to curb the effects of germ-releasing activities (e.g., face masks, gloves, hair nets, etc), and although employers require employees to wear CCE, the cost of contamination in the workplace remains high. Manual monitoring of employees, vendors, and visitors through close circuit camera or direct supervision is both expensive and subjective. The overall reporting of violations can be inaccurate and unverifiable.

There is a need for a system that accurately monitors individuals and equipment in the production area, to detect events that could contaminate or otherwise adversely affect product purity, functionality, appearance, safety, etc., to ensure that individuals in a production area wear required articles of CCE and to ensure that they do not interact with the production process in a manner that can spread disease, germs, and other contaminants, and/or to ensure that individuals do not contaminate a production area in a manner that negatively impacts product functionality and/or product appearance. There is a further need for contamination-control protocol in order to avoid damage to products and/or injury to the ultimate consumer of the product. There is also a need to warn and/or restrict individuals involved in high risk germ-releasing and germ-spreading activities and to mark food or other products as contaminated if the product is intended to be consumed free of contamination.

Similarly, there is a need for a system that accurately monitors and controls individuals as they work in a service environment, such as a hospital, school, restaurant, theater, retail store, etc., to ensure that service provider individuals in such a service area (i.e., a form of production area) do not interact with other individuals in a manner that can spread disease, germs, etc. It is further a need that the required contamination-control protocol is followed to avoid spreading of disease, germs, etc to other individuals in the service area.

SUMMARY

A first aspect of the invention is directed to an automated process for monitoring and controlling contamination activity in a production area. The process comprises (A) capturing image data from the production area over a period of time; (B) processing the image data with a computer to determine whether a contamination event has occurred in the production area, and (C) activating a contamination control device in accordance with the processing of the image data. The processing of the image data may optionally further comprise determining whether contamination control equipment is properly configured at the time of the contamination event.

In an embodiment, the processing of the image data further comprises processing the image data with a computer to determine: whether an individual is present within the production area, whether the individual has engaged in a contamination event while in the production area, whether an article of contamination control equipment is present in association with the individual during the contamination event; and whether the article of contamination control equipment is properly positioned and/or properly configured during the contamination event so that activation of the contamination control equipment acts to control the contaminant.

In an embodiment, the image data is processed to find an image of at least a portion of the individual present in the production area while the individual is in motion, with the image data being processed using a stabilization algorithm to determine whether the image data satisfies a threshold image value for a threshold time period. The threshold image value is a pre-determined minimum image value correlating with an absence of a contamination event by the individual and/or a pre-determined minimum image value correlating with the contamination control equipment being present and properly positioned while the individual is in the production area. The threshold time period is a pre-determined minimum time period that the threshold image value is satisfied. The activation of the contamination control device provides a positive indication of an absence of a contamination event by the individual.

In an embodiment, the image data is processed to find an image of at least a portion of the individual present in the production area while the individual is in motion, with the image data being processed using a stabilization algorithm to determine whether the image data satisfies a threshold image value for a threshold time period, with the threshold image value being a pre-determined minimum image value correlating with the occurrence of a contamination event by the individual and a pre-determined minimum image value correlating with the contamination control equipment being absent or improperly positioned during the contamination event. The threshold time period is a pre-determined minimum time period that the threshold image value is satisfied. The contamination control device is activated to provide a positive indication of a contamination event in the production area, due to a determination of both: (i) the occurrence of the contamination event in the production area, and (ii) the absence or improper positioning of the contamination control equipment during the contamination event.

In an embodiment, the contamination event is a germ-spreading event and the contamination control equipment comprises at least one member selected from the group consisting of a glove, a face mask, a suit, a gown, and a hair net, and the product article comprises food.

In an embodiment, the process further comprises processing the image data to determine the location in the production area of the individual when the contamination event occurs; and processing the image data to identify at least one potentially contaminated product article and/or identify at least one potentially contaminated production article that is within a contamination zone produced by the contamination event.

In an embodiment, the contamination control device comprises an automated report generator that processes the image data to generate a report including an identity of at least one potentially contaminated product article and/or at least one potentially contaminated production article within the contamination zone at the time of occurrence of the contamination event. The report may optionally include an image of the individual in the production area during the contamination event.

In an embodiment, a potentially contaminated product article and/or a potentially contaminated production article within the contamination zone is in motion during and/or after the contamination event, with the automated process further comprising processing the image data to track the location of the at least one potentially contaminated product article and/or potentially contaminated production article after the contamination event, so that identity and location of the potentially contaminated product article in the contamination zone and/or potentially contaminated production article in the contamination zone is known after the contamination event. The tracking of the at least one potentially contaminated product article and/or potentially contaminated production article is carried out using a stabilization algorithm to determine whether the image data satisfies a threshold image value for a threshold time period, with the threshold image value being a pre-determined minimum image value correlating with the identity of the at least one potentially contaminated product article and/or the at least one potentially contaminated production article. The threshold time period is a pre-determined minimum time period that the threshold image value is satisfied.

In an embodiment, the activating of the contamination control device comprises activating at least one member selected from group consisting of: (i) an alarm to notify the individual that the article of contamination control equipment is not present or is not properly positioned; (ii) an automated report generator that processes the image data to generate a report including information pertaining to the article of contamination control equipment not being present or not being properly positioned during the contamination event, and/or information indicating the work surface, article, food, or product that may be contaminated from the contamination event; (iii) equipment to decontaminate, move, reposition, shield, mark, track, and/or discard the at least one potentially contaminated product article and/or the at least one potentially contaminated production article within the contamination zone at the time of the contamination event.

In an embodiment, the automated report generator processes the image data to generate a report that includes an image of the individual in the work zone while the threshold image value is satisfied for the threshold time period, and a notation of a time at which the image was captured.

In an embodiment, the contamination event is a germ-spreading event. Such germ spreading events include coughing, sneezing, spitting, bleeding, vomiting, and excreting.

In an embodiment, the imaging sensor is a scanning imaging sensor configured and arranged to scan the production area. In an embodiment, the image data is captured by scanning at least a portion of the production area with a camera.

In an embodiment, at least one member selected from the production area, the individual, and the contamination control equipment has an RFID tag thereon.

In an embodiment, activating the contamination control device comprises at least one member selected from the group consisting of: (i) cutting off power to at least one machine in the production area, and (ii) interjecting a physical restraint or barrier between the individual and at least a portion of the production area, and (iii) sounding an alarm comprising at least one member selected from the group consisting of an audible alarm, a visual alarm, and a vibratory alarm, and (iv) generating and transmitting a report, with the transmission of the report comprising at least one member selected from the group consisting of transmission of an electronic report and transmission of a hard copy report.

A second aspect of the invention pertains to an automated system for monitoring and controlling contamination in a production area. The system comprises a computer, an image sensor in communication with the computer, and a computer-readable program code disposed on the computer. The image sensor is configured and arranged to capture image data of at least a portion of the production area. The computer-readable program code comprises: a first executable portion for processing the image data to produce an image of at least the portion of the production area captured by the image sensor, a second executable portion for processing image data and determining if a contamination event occurs within the portion of the production area captured by the image sensor, and a third executable portion for activating a contamination control device in accordance with the processing of the image data.

The second aspect can utilize any feature the various embodiments of the first aspect can utilize, and vice versa.

In an embodiment, the computer-readable program code further comprises an executable portion for processing the image data to determine whether an article of contamination control equipment is present and properly positioned.

In an embodiment, the computer-readable program code further comprises an executable portion for processing the image data to find an image of an individual in the production area, or a portion of an individual in the production area.

In an embodiment, the computer-readable program code comprises an executable portion for determining whether the individual has engaged in a contamination event while in the production area.

In an embodiment, the computer-readable program code further comprises an executable portion for processing the image data and determining whether an article of contamination control equipment is present and properly positioned on the individual in the production area.

In an embodiment, the computer-readable program code further comprises an executable portion for processing the image data to identify at least one potentially contaminated product article and/or identify at least one potentially contaminated product article that is within a contamination zone produced by the contamination event.

In an embodiment, the computer-readable program code further comprises an executable portion for tracking the at least one potentially contaminated product article that is within the contamination zone produced by the contamination event.

In an embodiment, the computer-readable program code further comprises an executable portion for marking the at least one potentially contaminated product article that is within the contamination zone produced by the contamination event.

In an embodiment, the computer-readable program code further comprises an executable portion for activating equipment to decontaminate, move, reposition, shield, or discard the at least one potentially contaminated product article and/or the at least one potentially contaminated production article within the contamination zone, in response to the contamination event.

In an embodiment, the computer-readable program code further comprises a stabilization algorithm to determine whether the image data satisfies a threshold image value for a threshold time period. The threshold image value is a pre-determined minimum image value correlating with an absence of a contamination event or a pre-determined minimum image value correlating with the presence of a contamination event. The threshold time period is a pre-determined minimum time period that the threshold image value is satisfied.

In an embodiment, the image sensor is a first image sensor in communication with the computer and the system further comprises a second image sensor in communication with the computer. The first image sensor captures image data from a first portion of the production area and the second image sensor captures image data from a second portion of the production area. Both the first and second image sensors are in communication with the computer, with the computer-readable program code processing image data from both the first image sensor and the second image sensor.

In an embodiment, the image sensor is a scanning imaging sensor configured and arranged to scan the production area.

In an embodiment, the automated system further comprises a data entry device in communication with the computer.

In an embodiment, the automated system further comprises a printer in communication with the computer, the printer being capable of printing a report of a determination of whether a contamination event has or has not occurred, and/or whether contamination control equipment is properly positioned on the individual in the production area.

In an embodiment, the computer-readable program code further comprises an executable portion for processing the image data captured over a time period, to find an image of an individual in motion (or portion of an individual in motion) in the image data captured by the image sensor, with the program code further comprising an executable portion for determining whether the individual has engaged in a contamination event while in the production area, and an executable portion for determining whether contamination control equipment is properly positioned on the individual in the production area. The computer-readable program code further comprises a stabilization algorithm to determine whether the image data satisfies a threshold image value for a threshold time period, with the threshold image value being a pre-determined minimum image value correlating with the presence of a contamination event, and the threshold time period being a pre-determined minimum time period that the threshold image value is satisfied. Optionally, the computer-readable program code further comprises an executable portion to identify at least one potentially contaminated product article within a contamination zone produced by the contamination event.

DETAILED DESCRIPTION

Figure 1:
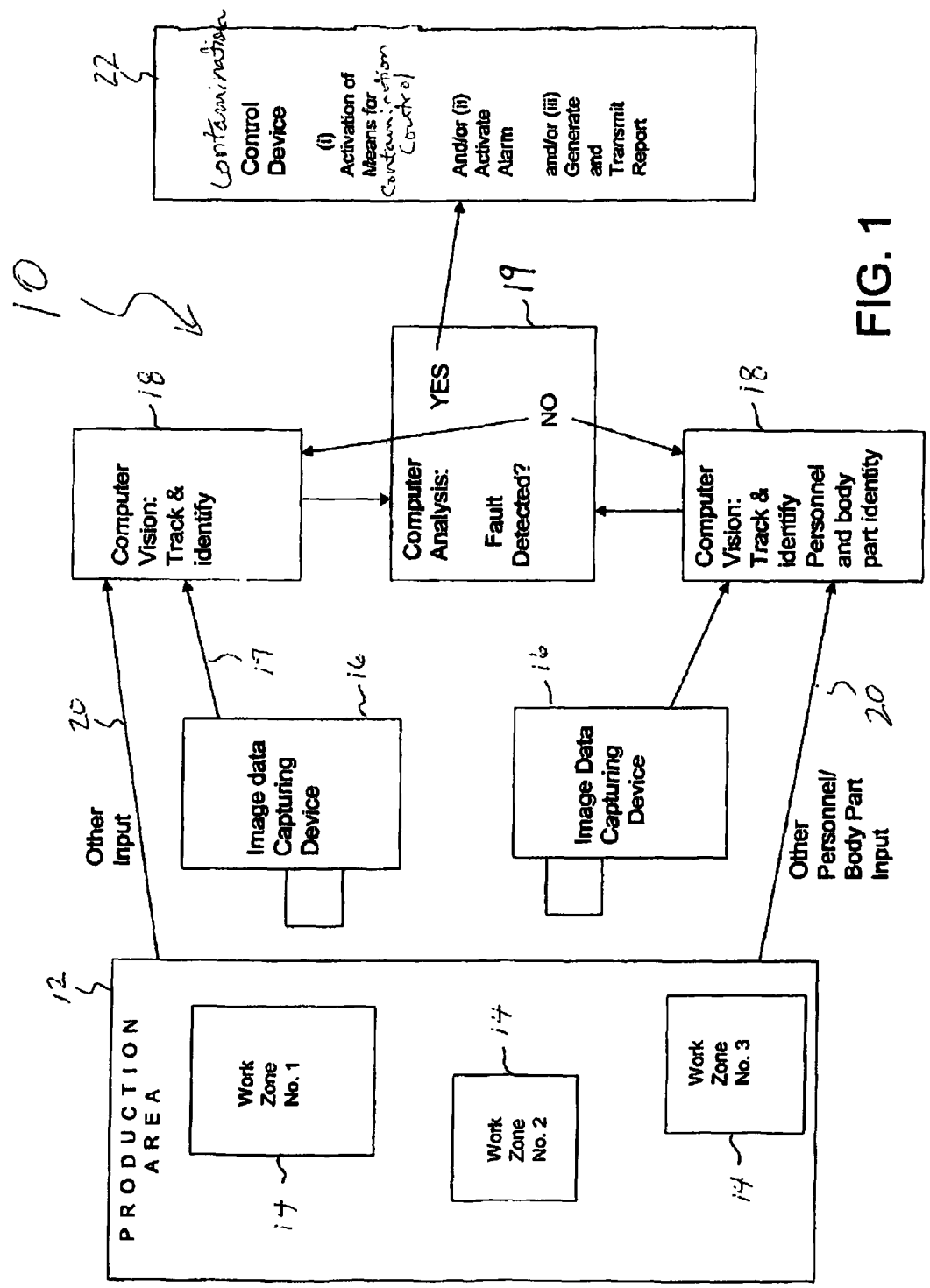
FIG. 1 is a schematic diagram illustrating an automated machine vision process and system for monitoring and controlling of contamination in a production area through the monitoring of and control of contamination events and, optionally, the monitoring and control of the associated wearing of one or more articles of CCE by one or more individuals in a production area.

As used herein, the phrase "automated process" is used with reference to processes utilizing computer vision and/or machine vision in obtaining and processing image data. The image data is captured using one or more image sensors in communication with a computer. While the process can be carried out using only image data, additional data can be input from machine-readable or human-readable sensors and identifiers, radio frequency identification transponder (RFID) or other transmitting sensors, time stamps or biometric identification, object recognition, texture definition, database management and other software, data interface equipment consisting of serial, parallel, or network communication, binary data such as switches, gates, push buttons, current sensors, as well as additional forms of data input. One or more computers can process image data and optionally other data from other sensors, identifiers, etc., using algorithms designed to determine whether the computer is to activate a control device, particularly a contamination control device (hereinafter "CC device").

As used herein, the phrases "image sensor" and "imaging sensor" refer to a component of a vision system that captures image data, e.g., a camera or other image capturing device. In computer vision and machine vision systems, one or more image sensors are configured and arranged to capture image data of one or more objects within the production area. Image sensors include analog video cameras, digital video cameras, color and monochrome cameras, closed-circuit television (CCTV) cameras, charge-coupled device (CCD) sensors, complementary metal oxide semiconductor (CMOS) sensors, analog and digital cameras, PC cameras, pan-tilt-zoom cameras (PTZ), web cameras, infra-red imaging devices, and any other devices that can capture image data. The selection of the particular camera type for a particular facility may be based on factors including environmental lighting conditions, the frame rate and data acquisition rate, and the ability to process data from the lens of the camera within the electronic circuitry of the camera control board, the size of the camera and associated electronics, the ease with which the camera can be mounted as well as powered, the lens attributes which are required based on the physical layout of the facility and the relative position of the camera to the objects, and the cost of the camera. Exemplary cameras that may be used in the practice of the invention are available from Sony such as Sony Handycam Camcorder model number DCR-SR80.

Image data can be captured and processed to monitor individuals, contamination control equipment, products, production equipment, as well the production area and the production environment. Image data can be processed in a manner to determine whether an article of contamination control equipment (hereinafter "CCE") is being properly worn by an individual. Upon determination that a required article of CCE is not present or is not properly positioned, the computer can be programmed to send a signal that automatically activates a CC device.

Since contamination events and other actions take place over a period of time, processing of image data to detect a contamination event and other actions occurring in the production area requires capturing image data over a period of time. Differences in location and/or conformation of objects as a function of time allows the computer to process image data in a manner that distinguishes moving objects from non-moving background. Image data can also be processed using one or more threshold values to determine whether a contamination event has occurred in violation of one or more predetermined standards for the production area, with activation of a CC device in the event that a contamination event is determined to have occurred.

The computer system, i.e., one or more computers, can be programmed to process the image data to identify individuals as well as other objects in motion, and separate the moving objects from the non-moving background images. The computer system can be programmed to distinguish images of individuals from images of other moving objects. The computer system can be programmed to process image data for individuals required to be wearing CCE, and determine whether an individual is wearing required CCE, as well as whether the CCE is properly positioned on the individual in the production area.

Computer-readable program codes include program modules, algorithms, rules, and combinations thereof. The computer system may include computer-readable program codes that process the image data of one or more objects being monitored, in order to perform one or more of the following functions: identifying an object being monitored; tracking an object as it moves within the production area; locating an object in the production area; and associating information with an object. The computer system may process image data utilizing program modules, algorithms, rules, and combinations thereof.

As used herein, the phrase "image value correlating with the identity of at least one potentially contaminated product article and/or at least one potentially contaminated production article" refers to the image of at least one product article or production article in the contamination zone at the time of, and after, the contamination event. If the product article and/or production article is in motion during and/or after the contamination event, the captured image data changes as a function of time. However, the changing image data is monitored so that the changing images remain correlated with the potentially contaminated article in motion, i.e., correlated with the identity of the article, whether the article is in motion or is not in motion during and after the contamination event.

As used herein, the tracking of a product article that was in the contamination zone, and the tracking of a production article that was in the contamination zone, is carried out using the image data captured by cameras and optionally other sensing devices, in combination with a computer programmed to take in the image data and monitor changes in the image data as the article moves through the production area.

Computer vision may utilize one or more of the following: camera, computer, object recognition and tracking using blob analysis, texture definition, data base management and other software, data interface equipment consisting of serial, parallel, or network communication, specific activity based, founding data originating from the person or CCE (containing information on the individual or the CCE), and integration of other discrete characterization data such as RFID tags, binary data such as switches, gates, push buttons, or current sensors.

The computer vision system may utilize an algorithm model or vision-based software to correctly identify a person from the environment. This may involve the use of multiple cameras and the geometric correlation of the perspective of a plurality of cameras having overlapping views or views from different perspectives. Algorithms such as the background subtraction method, Canny imaging methods, and Harris corner imaging methods may be used to allow for the overall visual features of a person, their eyes, ears, nose, head, arms, hand or other body part to be identified.

Using the same types of vision algorithms applied for tracking people, a contamination event can be identified and associated with an individual, a machine, or any other monitored item in the production area. The contamination event can also be identified and associated with an environment in which CCE is required. The tracking and monitoring of an individual can be carried out simultaneously with the evaluation of the individual for a contamination event (e.g., a germ-producing event) as well as the evaluation of any product or other article potentially contaminated by the contamination event, as well as the simultaneous evaluation of the presence and proper positioning (and proper activation, if necessary) of one or more articles of CCE. The coupling of data from auxiliary equipment from markers such as RFID tags, physical interface monitors, and electronic controls (such as in-line current sensing units) to the CCE and the person or other article within the production area provides additional monitoring capability.

The software's recognition of contamination events and other actions may trigger parent-child relationships to other pieces of equipment and products and the analysis of a continuous stream of data from the cameras may initiate additional correlations of the individual and contaminated products as the individual moves within a monitored area. The interface summary and detection data may be printed to a report, burned to an electronic chip, or compact disc or other storage device or stored in a computer database and referenced by a unique identifier including name, contamination event classification, CCE type, and/or location.

Image data can be processed using video content analysis (VCA) techniques. For a detailed discussion of suitable VCA techniques, see, for example, Nathanael Rota and Monique Thonnat, "Video Sequence Interpretation for Visual Surveillance," in Proc. of the 3d IEEE Int'l Workshop on Visual Surveillance, 59-67, Dublin, Ireland (Jul. 1, 2000), and Jonathan Owens and Andrew Hunter, "Application in the Self-Organizing Map to Trajectory Classification," in Proc. Of the 3d IEEE Int'l Workshop on Visual Surveillance, 77-83, Dublin, Ireland (Jul. 1, 2000), both of which are hereby incorporated by reference. Generally, the VCA techniques are employed to recognize various features in the images obtained by the image capture devices.

The computer system may use one or more Item Recognition Modules (IRM) to process image data for the recognition of a particular individual or other object in motion, and/or an article of CCE. In addition, the computer system may use one or more Location Recognition Module (LRM) to determine the location of a particular individual or other object in motion, or an article of CCE. In addition, the computer system may use one or more Movement Recognition Modules (MRM) to process movement data for the recognition of a particular individual or other object in motion, or article of CCE. The computer may use IRM in combination with LRM and/or MRM in identifying and tracking movements of particular individual or other object in motion, or article of CCE for the purpose of assessing velocity of movement and/or conformational movement characteristics, as well as in assessing whether contamination control requirements are being violated. The IRM, LRM, and MRM can be configured to operate independently or in conjunction with one another.

The image data can be analyzed using human classification techniques that can be employed for the purpose of confirming whether an object is a human, as well as for analyzing the facial features. Face detection may be performed in accordance with the teachings described in, for example, International Patent WO 9932959, entitled "Method and System for Gesture Based Option Selection", and Damian Lyons and Daniel Pelletier, "A line-Scan Computer vision Algorithm for Identifying Human Body Features," Gesture '99, 85-96 France (1999), Ming-Hsuan Yand and Narendra Ahuja, "Detecting Human Faces in Color Images," Proc. Of the 1998 IEEE Int'l Conf. on Image Processing (ICIP98), Vol. I, 127-130, (October 1998); and I. Haritaoglu, D. Harwood, L. Davis, "Hydra: Multiple People Detection and Tracking Using Silhouettes," Computer Vision and Pattern Recognition, Second Workshop of Video Surveillance (CVPR, 1999), each of which is hereby incorporated by reference, in its entirety. Face recognition may be performed on one of the faces detected in accordance with the teachings described in, for example, Antonio Colmenarez and Thomas Huang, "Maximum Likelihood Face Detection," $2^{nd}$ Int'l Conf. on Face and Gesture Recognition, 164-169, Killington, Vt. (Oct. 14-16, 1996), which is also incorporated by reference, in its entirety.

As used herein, the phrase "production area" refers to any area in which machines and/or individuals work in an environment to make any form of measurable progress. While a typical production area would be a factory in which articles of manufacture are being produced, the phrase "production area" includes restaurants, hospitals, gas stations, construction sites, offices, hospitals, etc., i.e., anywhere a product is being produced and/or a service is being rendered. The criteria for controlling contamination of a production area depend upon the particular nature of the production area, i.e., what articles are being produced and/or services offered, and the contamination control requirements associated with those products and/or services. Optionally, a production area can contain one or more work zones, with each work zone having different standards for the occurrence of a contamination event. The monitoring and control of contamination in different work zones can be carried out in a manner designed to monitor and control different kinds of contamination events in the different work zones.

The terms "contamination" and "contaminant" refer to any undesired substance or article released into the production area, i.e., any substance or article (including particulates) having the potential to adversely affect a product being produced, adversely affect the production equipment, adversely affect the production process, or adversely affect the production environment itself, i.e., floors, walls, ceiling, atmosphere, etc.

The phrases "contamination event" and "contamination-releasing event" and "contamination activity" refer to event(s) in which a contaminant is released into a production area in a manner so that it adversely affects a product, production equipment, the production process, or the production environment. Examples of contamination events include the release of germs by individuals in the production area, e.g., by coughing, sneezing, sweating, spitting, bleeding, vomiting, belching, crying, excreting, etc. Contamination events include other kinds of individual action in the production area, such as spilling, breaking, dropping, touching, breathing on, etc. Contamination events also include events that occur in the production area without involving the direct action of an individual, such as a pipe leaking or breaking with a resulting release of the contents, a light bulb exploding releasing glass fragments (and possibly additional contaminates) into the production area, and/or production equipment degrading or breaking in some manner that releases one or more substances, parts, or fragments so as to potentially contaminate product passing through a production line or production equipment operating in the production area. Contamination events also include actions outside the production area that cause the release of a contaminant into or within the production area, such as a fire or other event outside the production area releasing atmospheric particulates into the environment of the production area, vibration absorbed by the production area releasing particulates from one or more surfaces within the production area, a lightning strike into or near the production area causing a contaminate to be released into the production area, high winds buffeting the production area causing the release of particulates and/or fragments from one or more surfaces bounding the production area to within the production area, etc. The automated monitoring and control system can be designed to automatically detect, monitor, and control a wide variety of contaminants that may be released into the production area. As used herein, the phrase "germ-releasing event" refers to any event, gesture, movement by an individual in the production area that releases germs on or within the individual into the production area. As used herein, the phrase "germ-spreading event" refers to any means of spreading germs from one surface to another in the production area.

Contamination events include all events in which are detected and recognized by the automated monitoring and control system as spreading a contaminant into product, equipment, or the production environment. Contamination events are events that have been deemed to have a likelihood of releasing one or more contaminants into the production area in a manner that has a potentially adverse effect upon product being produced, production equipment, production process, production environment, etc.

A contamination event can be addressed by contamination control equipment. For example, a face mask can serve as contamination control to prevent a contamination event from a sneeze or cough, so long as the face mask is present and properly positioned on the individual during the sneeze or cough.

Automated contamination monitoring and control can be established for virtually all foreseeable contamination events. Different kinds of contamination events and different kinds of contamination require different means for monitoring and control thereof.

"Contamination control" is inclusive of actions designed to achieve immediate reduction, minimization, isolation or elimination of the contamination, as well as actions designed to achieve a more delayed reduction, minimization, or elimination of contamination. Actions providing relatively immediate contamination control, include, for example: (i) placing a shield around one or more products to prevent contamination from reaching the product(s), (ii) placing a shield around an individual to prevent contamination emitted by the individual from spreading within the production area, (iii) cutting off power to production equipment to allow the production area to be sterilized and contaminated product removed or decontaminated, before re-starting the production equipment, and (iv) the activation of an alarm upon the occurrence of the contamination event. Contamination control can also include tracking of contaminated or potentially contaminated products and/or production equipment and/or individuals, and can include marking tracked products and taking measures to dispose of, sanitize, or otherwise resolve the contamination of products, equipment, and individuals.

As used herein, the phrase "contamination control device" refers to any device designed to control one or more contaminants in the production area, i.e., to in some manner reduce, minimize, isolate, sterilize, or eliminate one or more contaminants in the production area. A contamination control device may also take action to control production equipment, products, and/or individuals within the production area. A contamination control device may take controlling action in advance of a contamination event or, more commonly, in response to the detection of a contamination event.

An example of contamination control actions designed to achieve a more delayed reduction, minimization, or elimination of contamination include, for example, the preparation of a report identifying a contamination event (or contamination event) in the production area. The action can optionally further include transmission of the report to production supervision and production management, as well as to the individual responsible for the contamination event. Thus, the phrase "contamination control device" is also inclusive of devices that take no action other than the generation of a report revealing the presence (or absence) of contamination events in a production area over a time period. Such a report is available to inform management of any contamination events that may have occurred (or the absence of such events), so that management may take appropriate action to minimize future contamination events and/or to control the impact of contamination events that have occurred in the past and/or maintain a desired minimum level of occurrence of contamination events. Of course, the contamination control device can include means for transmitting the report to management.

A contamination control device can be activated so that it acts in a manner "in accordance with" the processed image data. For example, if the image data shows no contamination event, the contamination control device could be a report showing no contamination event by the individual during the period in which the image data is captured. On the other hand, if the image data shows a contamination event, the system can activate a contamination control device that actively addresses the contamination with any active means of contamination control, as set forth above.

As used herein, the phrase "work zone" refers to a discrete area that can correspond with an entire production area, one or more discrete regions of a production area, or even an entire production area plus an additional area. Different regions within a production area can have different germ control and contamination control requirements. For example, a first work zone could include only a defined area immediately surrounding a particular cutting board or machine in a factory. The germ-releasing events and control requirements for the machine operator and others within a specified distance of the machine may be greater than the contamination control requirements just a few meters away from the machine. A factory can have many different work zones within a single production area, such as 2-100 work zones, 2-50 work zones, or 2-10 work zones. Alternatively, a factory can have uniform germ-releasing event characteristics or CCE requirements throughout the production area, which can be one single work zone.

As used herein, the phrase "contamination control equipment" (i.e., "CCE") refers to any article to be worn by an individual for the purpose of controlling the emission of germs from the individual into the production environment. As such, articles of CCE include face masks, suit, napkins, tissues, etc.

As used herein, the phrase "contamination control device" (i.e., "CC device") also includes any device that, when activated, is designed to prevent, reduce the likelihood of, or reduce the degree of, the release of germs from the individual into the production area. The CC device can be designed to immediately prevent the release of germs and/or reduce the likelihood of the release of germs, and/or reduce the degree of contamination released by the individual.

For example, the activation of the CC device when detecting a germ-releasing event could discontinue power to a machine, or interject a physical barrier or restraint between an individual and product that could be contaminated by germs. Alternatively, the CC device could provide a more delayed effect on prevention or reduction of contamination. For example, the CC device could be in the form of an alarm to alert one or more individuals of the germ contamination associated with the germ-releasing event within the production area. The individuals could be left to decide how to address the condition in response to the alarm. Alternatively, the CC device could generate and transmit a report to a production manager, agent, safety officer, etc., for the purpose of modifying behavior so that the presence of a germ-releasing event, absence of the required article of CCE, shipping of a germ contaminated article would be less likely to occur at present or in the future.

As used herein, the term "movement" includes movements of objects in which the location of the center of gravity of the individual or object changes, as well as movements in which the center of gravity does not change, but the conformation of the individual or object changes. Changes in the location of the center of gravity of an individual or object in an ascertainable time period correlate with the velocity of the individual or object. "Conformational movements" are movements in which there is a substantial change in the location of at least a portion of the individual or object, but only a small (or no) change in the location of the center of gravity of the individual or object.

The automated process for monitoring and controlling germ-releasing events and the germ contamination of food, products, or machinery in a production area utilizes algorithm-based computer vision to: (i) identify an individual or a portion of an individual; (ii) identify whether a germ-releasing event such as sneezing, coughing, vomiting, sweating, crying, bleeding, or spitting etc. has occurred, iii) a required article of CCE is present in association with the individual or the portion of the individual, and/or determine whether the individual or portion of the individual has the required article of CCE properly positioned thereon; identify whether a required article of CCE is present in association with the individual or the portion of the individual, and/or determine whether the individual or portion of the individual has the required article of CCE properly positioned thereon; (iv) send a signal to automatically activate a CC device in the event that a germ-releasing event has occurred and in some cases that the required article of CCE is not present in association with the individual or the portion of the individual, and/or that the required article of CCE is not properly positioned on the individual or portion of the individual, As used herein, the phrase "contamination zone" refers to a volume encompassing the location of the contamination event, within which volume product articles and processing articles are in close enough proximity to be at risk of contamination from the contamination event. Of course, the location, size, and shape of the contamination zone depend upon the nature of the contamination (including the size and type of contamination event), the nature of the product articles and production articles in the vicinity of the contamination event, and the environmental conditions surrounding the location at which the contamination event occurs.

One or more embodiments of the present invention now will be described with reference to the accompanying drawings, in which some, but not all embodiments of the invention are shown. The invention may be embodied in many different forms and should not be construed as limited to the embodiments set forth herein. Rather, these embodiments are provided so that this disclosure will satisfy applicable legal requirements. Like numbers refer to like elements throughout.

FIG. 1 is a schematic diagram illustrating an automated machine vision process and system 10 for monitoring and controlling contamination in a production area through the monitoring of contamination events such as sneezing, coughing, vomiting, sweating, crying, bleeding, spitting, pipe leakage, machine fragmentation, etc., control of the wearing of one or more articles of CCE by one or more individuals in the production area or presence of other CCE, the tracking of items contaminated by the contamination event, as well as controlling contamination of the production area including any products that may be contaminated, any production equipment that may be contaminated, and any portion of the production environment that may be contaminated.

The control of the contamination can take any of a wide variety of forms, including marking, shielding, and/or sanitizing any contaminated or potentially contaminated products and/or production equipment and/or portions of the production area. Contamination control can also be more long range control, such as by the preparation and transmission of a report of the contamination event and data related to the contamination event, including one or more images of the contamination event and/or one or more images of contaminated products, equipment, etc. Contamination control can also utilize marking and/or tracking of contaminated or potentially contaminated products and production equipment that are in motion in the production area.

Computer vision system 18 is set up and controlled to monitor production area 12 for the detection of contamination events. For example, computer vision system 18 captures and processes data related to one or more individuals for the detection of contamination events, and also captures and processes data related to whether the individuals are wearing CCE and whether the CCE is properly positioned on the individual. Alternatively or additionally, computer vision system 18 captures and processes data related to products and production equipment, and other items in the production area (e.g., utilities and other items) for a potential contamination event. For example, computer vision system 18 can also be set up to capture and process data related leakage of a product container or of a pipe carrying fluid within the production area, breakage of a part of a production machine, entry of a foreign substance (e.g., dust, smoke or other airborne particulates) into the atmosphere of the production area from outside the production area.

Production area 12 has multiple work zones 14 therein. Although image data capturing devices 16 (e.g., cameras) are shown outside of production area 12, they could be within production area 12. The one or more image data capturing devices 16 could be within production area 12 but not within any of work zones 14, or some or all image data capturing devices 16 could be within one or more of work zones 14. Image data capturing devices 16 provide image data input to one or more computer vision systems 18 with data tracking and identifying personnel or body parts and actions thereof including location in production area 12, as well as whether an individual is within one of work zones 14. In addition to data provided by image data capturing devices 16, other data can be provided to computer vision system(s) 18 via other data input means such as symbolic alpha, or numeric information embodied in or on a machine or machine-readable or human-readable identifier such as a tag or label (e.g., bar coded tag or label), a hole pattern, a radio frequency identification transponder (RFID) or other transmitting sensors, machine readable sensors, time stamps or biometric identification, CCE markers or designs or coloration, etc., as illustrated by other input data 20 from production area 12 as well as from items used in association with contamination events (e.g., napkins, tissues, etc).

The resulting automated process system 10 provides data that is compared to predetermined fault criteria programmed into the one or more fault-detection analysis computers 19. For example, the fault criteria can be programmed to be met if an individual, present in the production area 12 (and/or one or more of work zones 14), engages in a contamination event and is not wearing one or more properly-positioned articles of CCE required for the area and/or zone. If computer vision system 18 in combination with fault-detection computer 19 determines that the individual has engaged in a contamination event and that product, production equipment, or the production area are contaminated by the contamination event, data input from computer vision system 18 to fault-detection computer 19 can be programmed to cause fault-detection computer 19 to trigger contamination control device 22. Contamination control device 22 can take over one or more actions such as: (i) activating a contamination control means, (ii) activating an alarm, (iii) activating the generation and transmission of a report of a violation of contamination control protocol, (iv) activating a system to control, move, shield, sanitize, etc., a product or production article contaminated (or potentially contaminated) by a contamination event.

The automated monitoring and control process may utilize two or more computers. A first computer can serve to process the image data with respect to whether, for example, an individual is present, whether the individual engages in a contamination event, whether the individual is wearing an article of contamination control equipment, whether the contamination equipment is properly positioned on the individual. A second computer can process the data to conduct the fault-detection analysis and the resulting determination of whether to activate the contamination control device, based on the data from the first computer.

If the automated process is directed to the presence of a contamination event that is a potential germ-releasing event such as such as sneezing, coughing, vomiting, sweating, crying, bleeding, or spitting etc. (or any other contamination event), and proper germ-containment, for example, by use of a face mask, the machine vision system can be designed to view the scene and detect the face of an individual and perform segmentation based on proportionality to find the eyes, arms, legs, back, and waist of an individual and the corresponding movements attributable to a germ-releasing event. The machine vision system can be designed to find features associated with the germ-releasing event (including color mismatch when eyes are closed and arms are moved, etc) and can be designed to remove non-moving objects, and zoom and/or read information on associated objects or persons and activate electromechanical circuit(s).

If the automated process is directed to the presence and proper use of a facemask (or any other form of germ-containment equipment for the body), the machine vision system can be designed to view the scene and perform background subtraction and detect the face of an individual, and perform segmentation based on proportionality to find the arms of the individual, and perform segmentation based on proportionality to find the hands of the individual. The machine vision system can be designed to find features associated with gloves, including color mismatch, etc. The machine vision system can be designed to find features associated with one or more gloves (including color mismatch, etc) and can be designed to remove non-moving objects and zoom and/or read information on associated objects or individuals, and activate electromechanical circuit(s).

If the automated process is directed to the presence of an article that may be contaminated by the germ-releasing event (or any other contamination event), the machine vision system can be designed to view the scene and perform background subtraction, color detection, edge detection, and other techniques to characterize and match an object to a database of objects or to create a new database describing the object in order to fully track and activate electromechanical circuit(s) such as washing devices (i.e., on cutting boards), conveyor diverters, waste receptacles, wrapping machines, laser markers, inkjet markers etc.

Figure 2:
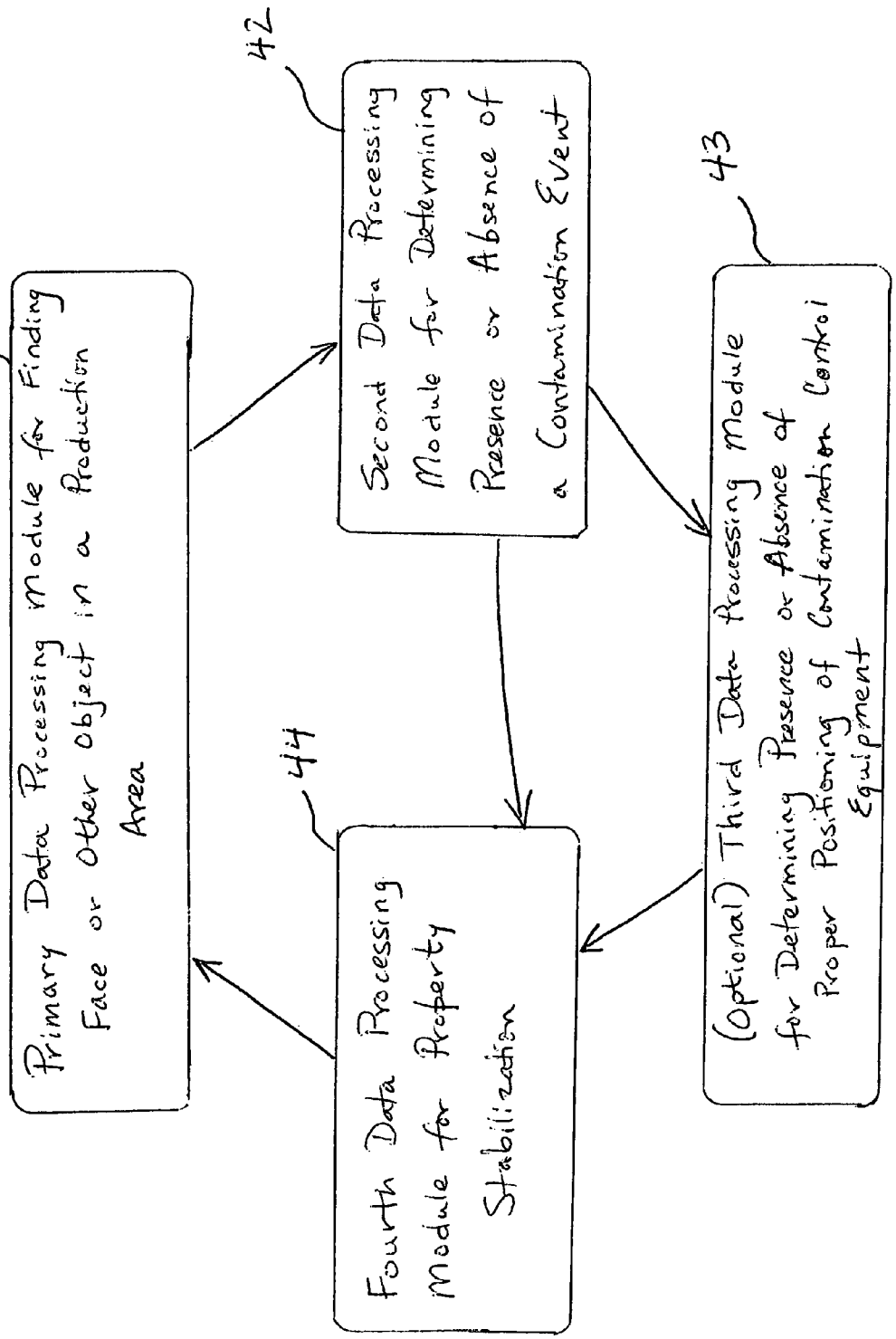
FIG. 2 is a representative schematic of a loop process for determining whether one or more persons or other objects in a production area are involved in contamination activity and/or have CCE properly positioned.

FIG. 2 illustrates a representative schematic of a loop process for determining whether a one or more persons in a production area are involved in a contamination event. The process of FIG. 2 includes: (i) a first data processing module 40 for finding a moving face, the facial features such as nose, ears, eyes, mouth, and other body parts such as arms, legs, waist, back, and neck within a production area, (ii) a second data processing module 42 for determining the presence or absence of a contamination event, (iii) a third data processing module 43 (optional) for determining the presence or absence of CCE such as a face mask on the associated face, as well as whether the CCE is properly positioned on the face or body, and (iv) a fourth data processing module 44 which utilizes a stabilization algorithm that tracks the face and body within the production area to ensure consistent data reporting.

Stabilization algorithm 44 completes a data processing feedback loop to prevent "false positives" from occurring. In the absence of stabilization algorithm 44, it can be difficult to set up the image capturing device and associated primary data processing module 40 and second processing module 42 so that together they consistently maintain an accurate determination of the presence of a contamination event and/or absence of properly-positioned CCE on an individual in motion in the production area. The motion of the face and body, the motion of other objects in the production area, and various other factors have been found to make it difficult to consistently make accurate determinations of the presence and placement of a germ-releasing event or other contamination event in the production area. As a result, inaccurate conclusions of non-compliance (i.e., "false positives") have been found to occur at a high rate, particularly when image data is being captured at a rate of, for example, 50 images per second. Single occurrences of images which show the presence of a germ-releasing event characteristic such a droplet of liquid falling from the vicinity of a face but which are inaccurately assessed by the data processing to be in the absence of CCE, can soar to thousands per hour. For example, as applied to a germ-releasing event by an individual, the stabilization algorithm of fourth data processing module 44 requires a combination of (a) assessment of a pre-determined quality of image (i.e., a minimum image value) associated with the face and body in the absence of a germ-releasing event and/or properly positioned CCE, and that this quality of image be present for at least a pre-determined minimum time period, before the system reports a germ-releasing contamination event and an associated CCE non-compliance event. In this manner, the process can be carried out using a stabilization algorithm that reduces the occurrence of a false positive to, for example, less than 0.1 percent of all determinations of non-compliance determinations. In addition, the images can be processed so that an image having a very high image quality correlating with non-compliance can be saved as a record of the non-compliance event, e.g., for a report directed to a non-compliance event and/or a contamination event. Optionally, it can have the date, hour, and location provided therewith, together with other data such as the duration of the period of non-compliance, etc. The process loop of FIG. 2, and the use of a stabilization algorithm can also be applied to products in motion, production equipment in motion, and even stationary portions of the production environment.

The first step in the process of monitoring and controlling contamination in a production area associated with a germ-releasing event is to find the image of a face and the body in motion in a production area. This can be carried out by using Haar-like feature detection. Alternatively, the number of skin pixels within a face region can be counted in assessing that a particular image is that of a face. In a third method, an image is determined to be something other than a face if dividing the number of skin pixels by the number of pixels in the face region produces a result less than a threshold value, otherwise it is a face.

Finding facial images of one or more individuals in a production area can be reasonably limited to finding images of faces in motion in the production area. This can be performed by computing the difference between the image of the face and the background image, in which:

$$Dif=\Sigma(\text{within region})|I-B,$$

Where I is object image, and B is background image. The image can be judged as non-moving if Dif is less than a pre-determined threshold. The background image can be assessed using low pass filtering over time, in which:

$$B=\tau B+(1-\tau)I,$$

Where $\tau$ is a predetermined time constant, B is a low pass filtered background image, and I is an image.

Figure 3:
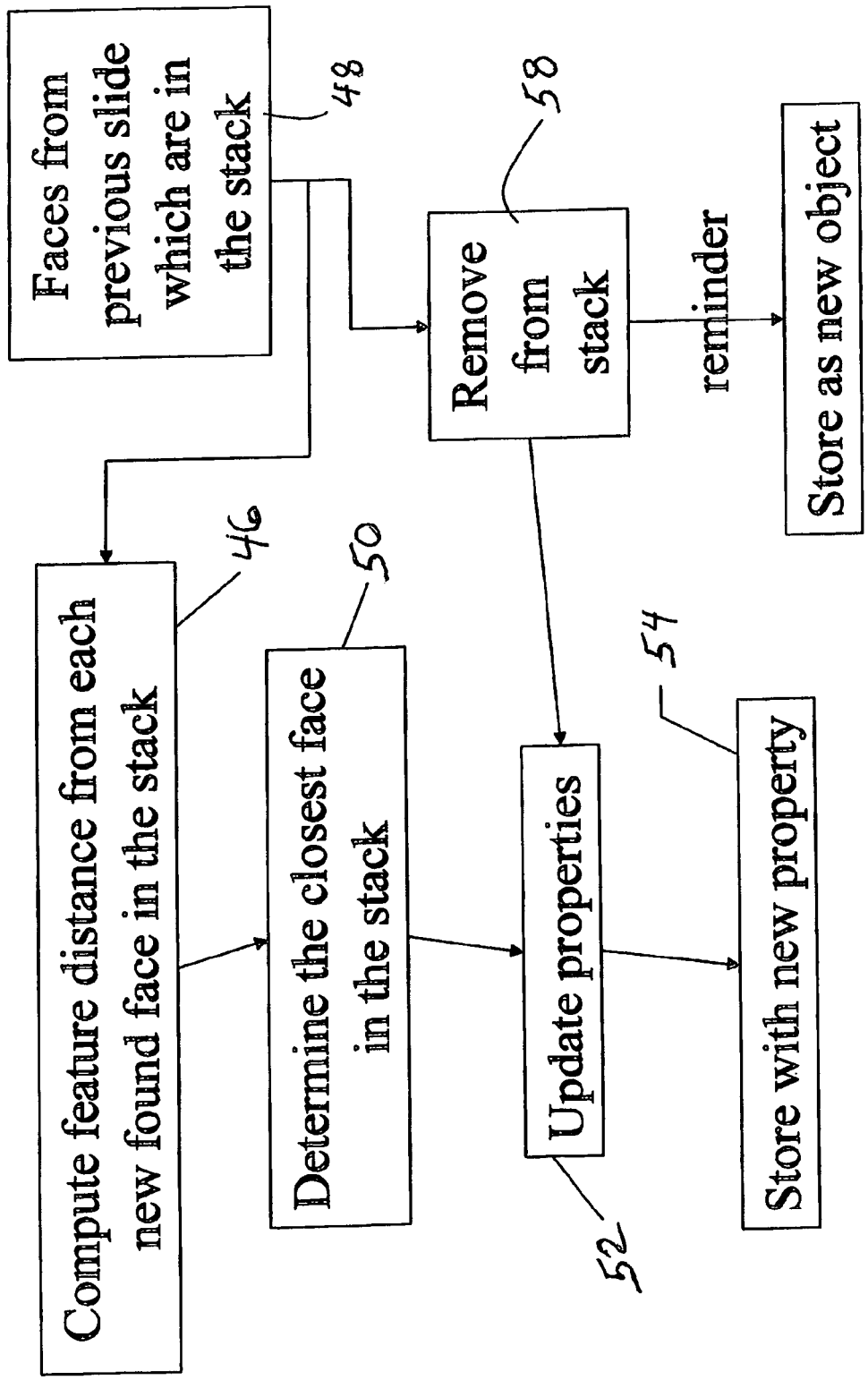
FIG. 3 is a representative schematic of a process for tracking images of individuals, or particular portions of individuals, in a production environment.

FIG. 3 illustrates a second step in the process, i.e., the step of tracking individual faces in the production area. As shown in FIG. 3 computation is made of the location of each face of the current image (46) and the locations of the features of the known faces in the previous image (48), i.e., distances are computed between each of the faces of the current image and the faces known from the image immediately preceding in time. Determinations are made as to which faces are closest to one another (50) between the faces in current image (46) and the faces in the immediately prior image (48). The speed of imaging is likely high enough (e.g., 200 milliseconds between images) that the likelihood is greatest that closest faces in the respective current and prior images in fact represent the same face. Locations and feature properties are then updated for the new image (52), and the new locations properties are stored (54). The old image of the production area including the old faces (48), can then be removed from the stack (58) (i.e., group) of closest faces in the current image (52), with faces of the new image then being stored together with the storage their new properties (54). A "reminder" is provided of the removal of the prior image of the old faces.

The computation of feature distances can be carried out by evaluation of differences in facial position ($y_1$), differences in face size ($y_2$), and differences in color histogram differences ($y_3$). Observation of facial features such as relative eye position and closure, mouth opening, cheek movement, head position can be used to determine if a germ-releasing event is about to occur, or has occurred. Feature distance D can be determined as:

$$D=y_1^2\sigma_{y1}^2+y_2^2\sigma_{y2}^2+y_3^2\sigma_{y3}^2$$

where $\sigma_{y1}^2$, $\sigma_{y2}^2$, $\sigma_{y3}^2$ are pre-determined variances obtained from samples of the same object in continuous (i.e., successive) frames. Properties can then be updated by measurement of measurement of the image life, i.e., by measurement of how long the image has been successfully tracked, by measurement of a low pass filtered determination of the CCE "on/off value" of the face, and by characterization of the features of the face, including position, size, and color histogram. Properties can be updated by the Increment Life value if the tracked face is associated with the face found in the current frame, as well as by Decrement Life if no face is associated to this tracked face. An example of determination of the low pass filter "on/off value" of the CCE on the face is as follows:

$$LPF \leftarrow \tau LPF+(1-\tau)\text{status}$$

here $\tau$ is a predetermined time constant.

Figure 4:
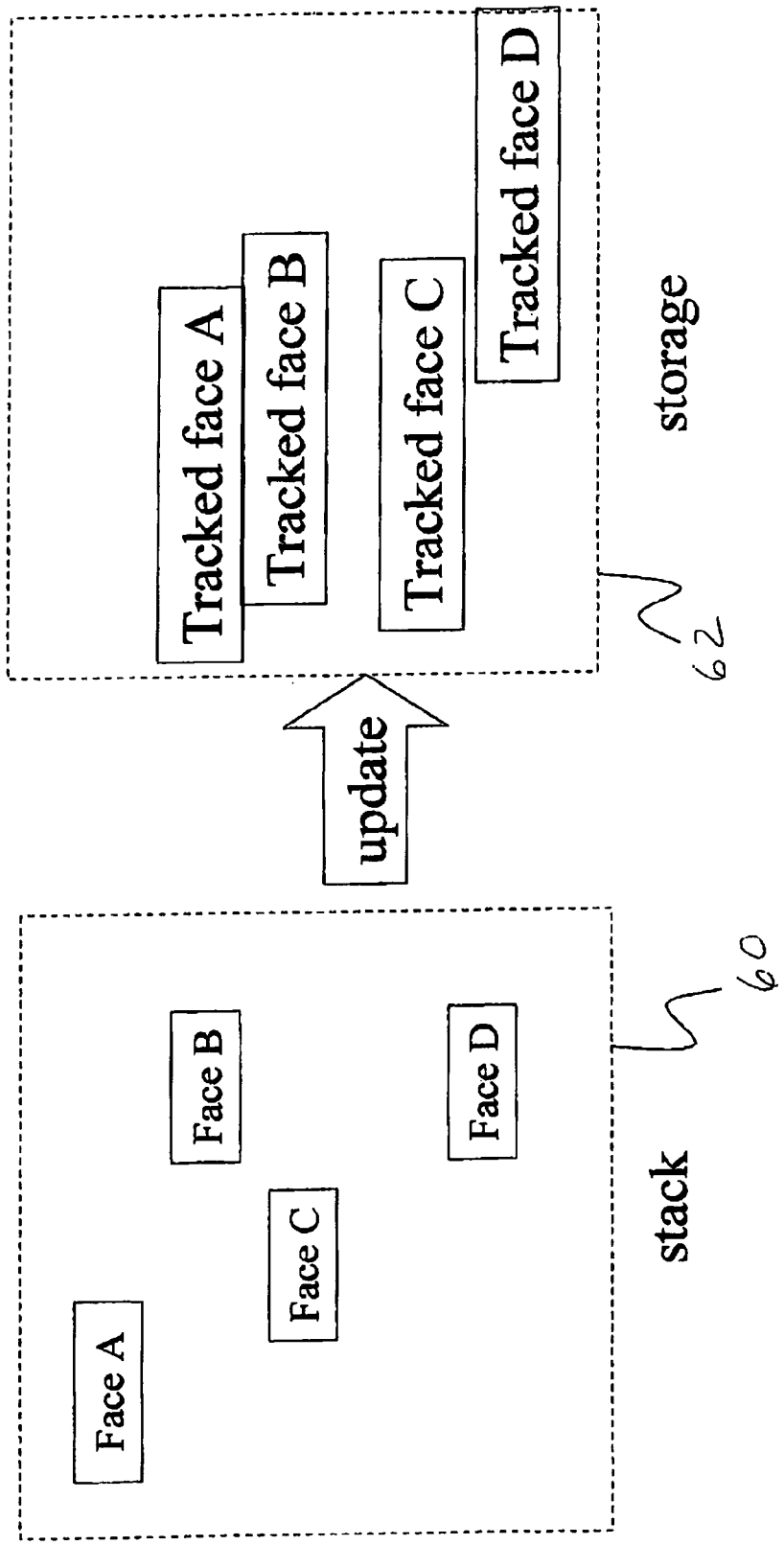
FIG. 4 is an illustration of the tracking of a plurality of faces and of the associated body in a given image from the production area.

FIG. 4 is an illustration of the tracking of a plurality of faces in a given image from the production area. Image 60 is taken at $T_1$. In image 60, Face A, Face B, Face C, and Face D appear at particular locations. Image 62 is taken at time $T_2$, a fraction of a second after $T_1$. Image 62 shows tracked Face A, tracked Face B, tracked Face C, and tracked Face D at particular locations of image 62. While tracked Face A and tracked Face D are in approximately the same locations at $T_2$ as at $T_1$, tracked Faces B and C appear in different positions at $T_2$, showing their relative movement between $T_1$ and $T_2$. As described above, the properties of each of Faces A-D include their "life" (i.e., how long they have been present in the image, including how long they have been present at or near their current location), the image value of the low pass filter CCE on/off value, their location (i.e., position), size, and color histogram. The update of the properties can be assessed by the increment life value, the decrement life, and the low pass filter on/off value, as described above.

Subsequently or in parallel an algorithm consisting of several modules assists in determining whether a germ-releasing event occurs, specifically: (a) a primary module that finds a moving object from a background within a work environment; (b) a secondary algorithm that finds an arm or other body part blob from the primary object; (c) a judgment algorithm that determines whether the blob has moved in relative position to other body parts or to the face in a time period or a manner characteristic of a germ-releasing event; and (d) a optional stabilization algorithm using tracking and time life to ensure accurate reporting.

Figure 5:
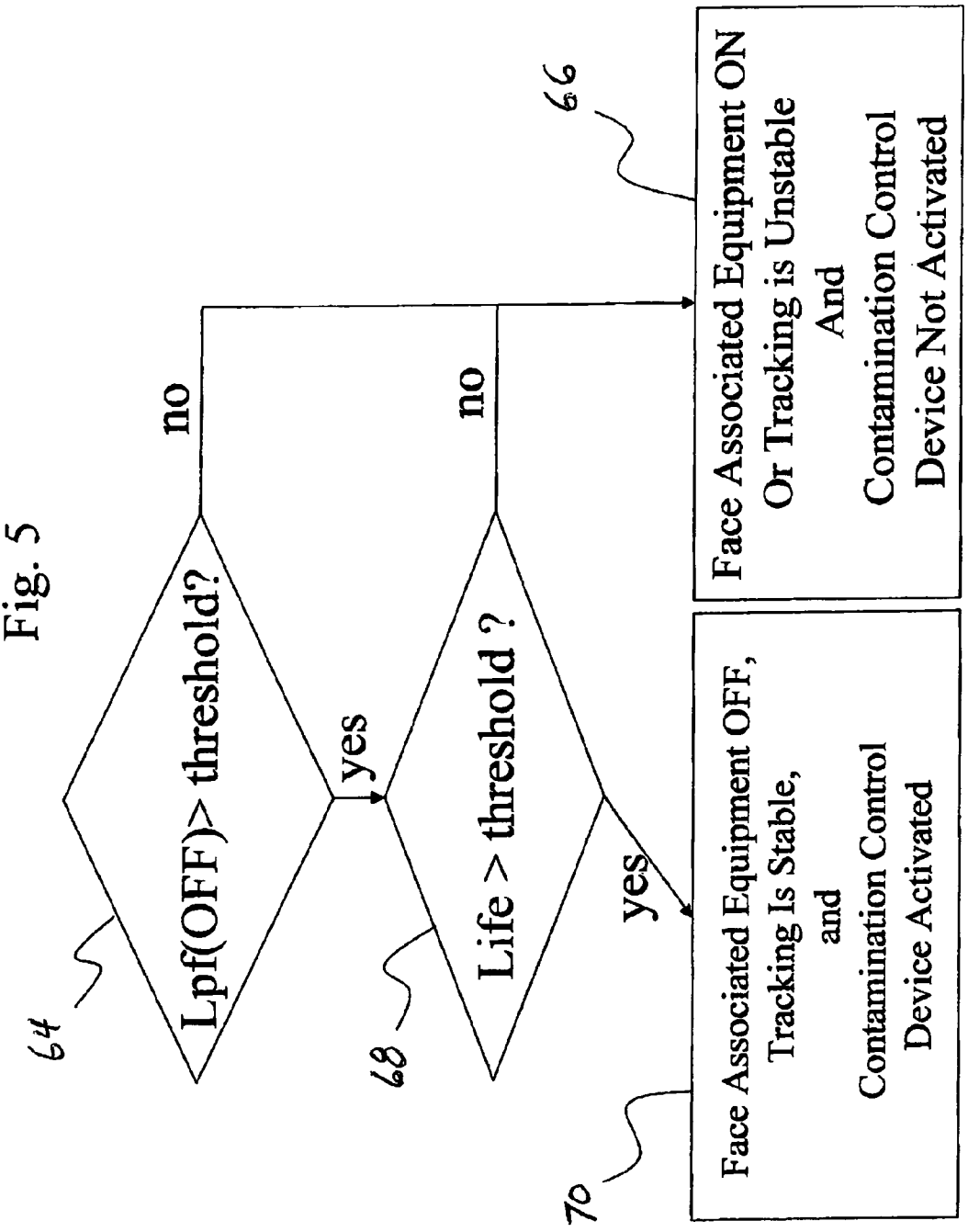
FIG. 5 is a representative schematic of the overall process for determining whether a tracked face and associated body is engaged in contamination activity and if the individual or face is wearing an article of CCE.

FIG. 5 is a representative schematic of the overall process for determining whether a tracked face is wearing an article of CCE. This process can be used in combination with the process used to determine if a germ-releasing event has or is about to occur to activate an electromechanical circuit(s) or CC device. This is the portion of the process and system that are designed to provide a data feedback loop to prevent "false positives" from occurring. In short, the feedback loop of the stabilization algorithm is set up to determine, with a high degree of accuracy, whether the face actually is wearing a required article of CCE in a manner conforming to contamination protocol within the production area. Without the use of the stabilization algorithm, a multitude of false positives have been found to occur when using image capturing and processing of faces in motion in a production area. This same kind of algorithm can be used to determine whether a contamination event has occurred.

In FIG. 5, each tracked face is assessed using a low pass filter (64), assessing whether the image value corresponds with the face properly wearing the required article of CCE, or not properly wearing the required article of CCE. A pre-determined image value threshold is used in processing the image of the tracked face. If the image of the tracked face is such that the assessed image value is less than the threshold image value, the image is assessed as either being unstable or that the required article of CCE is being properly worn by the face (66). In such an instance, no CC device is activated when a germ-releasing event occurs (66).

However, if the image value threshold is met during the low pass filter processing of the image of the tracked face (64), the processing is continued by assessing whether the time period over which the image value threshold is met is a time period that meets or exceeds a pre-determined threshold time period (68). If the image value threshold has not been met for the duration of the threshold time period, the result is that no CC device is activated (66). However, if the threshold image value is satisfied for the threshold time period, and a germ-releasing event has been determined to have occurred, a signal is sent that the face-associated CCE is "off" and that tracking is stable (70), with the result that a CC device is activated (70) in addition to any object or food tracking that may occur to mitigate the effect of the germ-releasing event.

Figure 6:
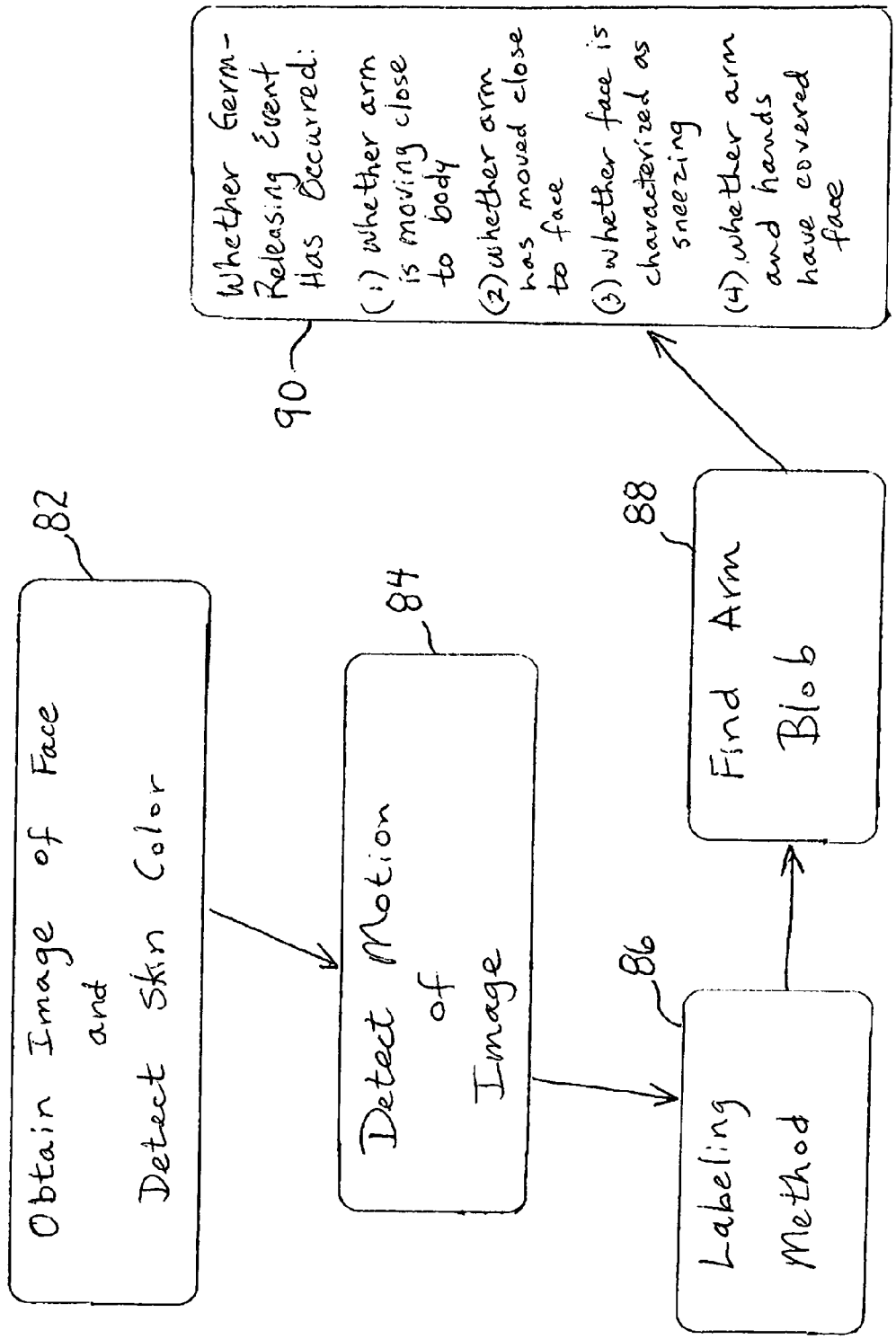
FIG. 6 is a schematic diagram illustrating an automated machine vision process and system for monitoring, controlling, and tracking contamination activities and the monitoring and controlling of the products or manufacturing process contaminated by the contamination activity in a production area through the monitoring of behavior, articles such as food or other products, and/or the wearing of one or more CCE by individuals in the production area.

FIG. 6 is a schematic of an automated process for detecting sneezing using a computer algorithm further coupled to camera and computer hardware. The algorithm is carried out by obtaining an image of the face and detecting skin color (82) in the image, followed by detecting motion (84) of the image, followed by a labeling method (86), followed by finding an arm blob (88), followed by judging whether an arm has moved close to the face, whether the face can be characterized as sneezing, and whether the arm and hands have covered the face to detect a germ-releasing event (90).

Skin color detection can be assessed as follows. First, for each pixel $p_1$=[R G B] and $p_2$=[R G B], pixel distance d is defined as $$d=(p_1-p_2)'\Sigma(p_1-p_2)$$

where $\Sigma$ is a matrix, in which inverse of covariance matrix is often used. N of pre-determined pixel sample represents skin: $(s_1, s_2, s_3, \ldots, s_N)$. Pixel distance $(d_1, d_2, d_3, \ldots, d_N)$ is computed from each pre-determined pixel $(s_1, s_2, s_3, \ldots, s_N)$. The minimum distance within N set of distances is found using: $d_{min}=\min\{d_1, d_2, d_3, \ldots, d_N\}$. Thresholding can be carried out using a pre-determined value th. If the distance is smaller than th, the pixel is skin, otherwise, the pixel is not skin.

Another method of skin color detection, which is faster, utilizes color vector analysis wherein p=[R G B], with pre-determined vectors $a_1, a_2, a_3, \ldots$ p is skin pixel if $$(a_1'p<th_1) \cap (a_2'p<th_2) \cap (a_3'p<th_3) \cap \ldots$$

Motion can be detected using a motion subtraction method. Motion exists if:

$$\Sigma_{(region\ of\ interest)}\{|I_n(x,y)-I_{n-T}(x,y)|\}>\text{threshold}$$

Most image processing cameras have this function. Motion detector devices can also be used.

The labeling method can be carried out by obtaining a blob from a binary image. The arm and hand blob can be found by finding the closest blob to a pre-determined object. Features include the size and the aspect ratio (i.e., ratio of horizontal to vertical size), with the blob being approximated as an ellipse, with the aspect ratio being the ratio of the long radius to the short radius.

The extraction of features from each blob is carried out by determining the long radius of the fitted ellipse, determining the short radius of fitted ellipse, determining the distance from a model contour by (a) fining the closest point in the object contour from model contour, and (b) summing the distances.

The smallest feature distance is determined by assessing the blob feature as:

$$x=(1,x_1,x_2,x_3,\ldots)^T,$$

assessing the model feature as:

$$y=(1,y_1,y_2,y_3,\ldots)^T,$$

and assessing the feature distance as:

$$d=(x-y)^T M(x-y).$$

Since there can be more than one model, find minimum of d. M is matrix, often used as inverse covariance.

Judging whether the smallest feature distance is less than the threshold value can be carried out as follows:

if $(x_1>th_1)$ and $(x_2<th_2)$ and $(x_3<th_3)$, then the arm and hand is determined to be on the face. In addition, a minimum time threshold must be determined and achieved as most germ-releasing events occur in quick motions. Otherwise, the germ-releasing event of sneezing is determined to not have occurred.

Tracking a hand or arm blob and maintaining stable properties of a hand, arm, waist, legs, and back with respect to a face and in addition to an associated CCE is important so that these properties can be used to make consistent determinations of whether a germ-releasing event has occurred; this can be carried out as follows: Sequence breaks are found by supposing $t_0, t_1, t_2, \ldots$ are instances when a motion is detected. If $(t_{n+1}-t_n)>\text{threshold}$, then there is a sequence break between $t_{n+1}$ and $t_n$. Otherwise, $t_{n+1}$ and $t_n$ are in the same sequence. The results are grouped by sequence. Focusing on each sequence, count the number of motions in which hands and mouth are in contact over a period of time. Disconnect time OFF images ($=N_{OFF}$). If $N_{OFF}>\text{threshold}$, then output warning with image and track any objects in proximity to the individual.

A horizontal edge under the eyes can also be assessed, to determine the opening or closing of eyes during a germ-producing event. The existence of an edge, and the strength of the edge located pre-determined position under the eyes can be measured and compared to sequence of facial images during a germ-releasing event such as sneezing or coughing. This can be assessed as follows:

$$x_3=|I_1-I_2|$$

where $I_1, I_2$ are pixel intensity located below eyes, with $I_1$ and $I_2$ being on the same horizontal axis but on different vertical axes.

Skin color can also be assessed as an indicator of whether a germ-releasing event has occurred as relative to moisture or liquid that may be positioned on or near the face, by determination of the ratio of pixels within skin color range or clear/white in pre-determined range, relative to the face, e.g., where $x_4$=number of skin color pixels.

Skin color detection can be assessed as follows. First, for each pixel $p_1$=[R G B] and $p_2$=[R G B], pixel distance d is defined as $$d=(p_1-p_2)'\Sigma(p_1-P_2)$$

where $\Sigma$ is a matrix, in which inverse of covariance matrix is often used. N of pre-determined pixel sample represents skin: $(s_1, s_2, s_3, \ldots, s_N)$. Pixel distance $(d_1, d_2, d_3, \ldots, d_N)$ is computed from each pre-determined pixel $(s_1, s_2, s_3, \ldots, s_N)$. The minimum distance within N set of distances is found using: $d_{min}=\min\{d_1, d_2, d_3, \ldots, d_N\}$. Thresholding can be carried out using a pre-determined value th. If the distance is smaller than th, the pixel is skin, otherwise, the pixel is not skin.

Another method of skin or saliva color detection, which is faster, utilizes color vector analysis wherein p=[R G B], with pre-determined vectors $a_1, a_2, a^3, \ldots$ p is skin pixel if $$(a_1'p<th_1) \cap (a_2'p<th_2) \cap (a_3'p<th_3) \cap \ldots$$

In determining whether a germ-releasing event has occurred either of the following methods can be used. Using simple thresholding, assume features $x_1, x_2, x_3, x_4$ and pre-determined threshold $th_1, th_2, th_3, th_4$, judge face-associated germ-releasing event as "ON" if:

$$(x_1>th_1) \cap (x_2>th_2) \cap (x_3>th_3) \cap (x_4>th_4)$$

Otherwise, face-associated CCE is judged as "OFF".

The second method for determining whether the face associated germ-releasing event is "ON" or "OFF" utilizes Bayesian classifier:

$$x=[x_1 x_2 x_3 x_4]^T$$

Face-associated germ-releasing event is judged as "ON" if:

$$p_{ON}(x) > p_{OFF}(x)$$

where $p_{ON}(x)$ and $p_{OFF}(x)$ are probability functions predetermined by samples. Normal distribution is assumed.

Example

As an example, a cutting board is located at a sandwich making station. The sandwich-maker is located at the cutting board and is monitored by a video camera such as, e.g., TrendNet® Model TV IP110 internet camera server network camera. The camera sends a visual data wirelessly via a router such as, e.g., NETGEAR®—RangeMax 802.11g Wireless Router, model WPN824, available from Best Buy, P.O. Box 9312, Minneapolis, Minn. 55440, to a computer such as, e.g., eMachines®—Netbook with Intel® Atom™ Processor, Model: EM250-1915, also available from Best Buy. The computer processes the data in a near real time manner to determine if the sandwich-maker is engaged in a germ-releasing event such as coughing or sneezing and in some cases if the event was accompanied by the use of a CCE such as a face mask. The output signal from the computer controls light emitting diodes embedded within the cutting board. The cutting board, made with food-grade polyethylene, may have light emitting diodes embedded in a corner, overlaid with a translucent printing identifying a warning symbol to indicate a germ-releasing event. Additional signal-receiving circuitry may be embedded in the cutting board so that a signal from the transmitter at the control computer can be received, further illuminating the board in the proper location to help warn the sandwich maker of any contamination-prevention requirement being violated.

In a similar manner, other items such as conveyors or bowls can be fitted with warning circuitry and light emitting diodes including colored lights to further help identify product or food that has been exposed to a germ-releasing event. For example, a flashing red light may indicate that food should not be eaten. Warning lights may be positioned independently in locations easily viewed by workers and managers. In some cases, the lights may be accompanied with acoustics including warning messages. A sign may have back-lit lettering such as "Don't cough near the cutting board". These signs may be activated by the computer vision system as described above when a fault is detected.

Similarly, signs may be located at a blender to identify if a batch of food has been contaminated by a germ-releasing event and a relay may be activated to shut the blender down. The occurrence of such an event, left undetected, can contaminate a large number of people and food products. A machine vision safety system can be used to identify the error when it occurs, as well as identifying the contaminated products prior to distribution and further activate auxiliary monitoring systems such as hyper spectral imaging cameras or wash solutions.

For example, if a sandwich maker coughs in a bowl of lettuce and is not wearing a face mask, the sandwich-maker can be identified when he touches a sandwich or edible product, and the product may be tracked through to its wrapping or packaging state. Prior to delivery to the customer, the package may be sent through a printing, labeling, or laser marking station and the wrapping or package marked or labeled with words or symbols to convey "contaminated food" or "do not use". In some cases, the sandwich or food may be placed on a conveyor for transit and an electromechanical or pneumatic system may divert the contaminated product to a disposal or a cleaning station. By the same token, food handled safely may be actively placed in a "safe zone" or labeled "handled safely".

In an environment in which multiple individuals are being monitored via a single camera, the control of lights or other items may require additional identifying symbols to be associated to the individual or item. In some cases a warning light may be installed within a mechanical fixture used to hold food which may be activated to identify that the food hanging, contained, attached, or associated to the fixture has been handled by an operator that engaged in a germ-releasing event such as sneezing, coughing, vomiting, bleeding, sweating, or spitting. As an example, consider a rack holding sausage. Above each hook a small light emitting diode is affixed and each hook is connected to a sensor and that detects when a sausage is added or loaded to the cart. Consider a sausage maker who has sneezed into the extruder. When the sausage-maker and the sausage, now identified by the algorithms as having engaged in a germ-releasing event, approach the cart, a warning status alarm is transmitted to the cart and a flashing light above the cart will warn that the sausage is unfit for sale.

Similarly to the above, the safety system may detect that a worker has coughed on food prior to, in transit to, or while the food is on a cart. The cart can be equipped with a warning light that is activated to allow for the identification of contaminated product. This system may also be used in hospitals to prevent the spread of germs from one location to another.

Once the system has determined that a safety violation has occurred a digital output from the computer is obtained. Typically, a +/−5V or +/−12V output is obtained from the controlling computer using USB, Ethernet, or RS-232 ports. This signal may be further modulated with codes corresponding to the individual in violation, the location or station in violation, the product that has been contaminated with the associated tracking data with the speed or translation data. As an example this signal could be used to drive an operational amplifier transistor circuit and then further control directly a timing, auditory, lighting, or electromechanical circuit. In some cases, the +/−5V or +/−12V electrical output signal could be used to drive a radio frequency transmitter that could modulate a receiving antenna and circuit. This circuit may be selective with regard to which light, auditory signal, electromechanical system, or timing circuit is activated depending on the transmitted codes.

Although the present invention has been described with reference to the preferred embodiments, it is to be understood that modifications and variations of the invention exist without departing from the principles and scope of the invention, as those skilled in the art will readily understand. Accordingly, such modifications are in accordance with the claims set forth below.

What is claimed is:

1. An automated process for monitoring and controlling contamination activity in a production area, comprising:
(A) capturing image data from the production area over a period of time;
(B) processing the image data with a computer to determine whether a contamination event has occurred in the production area; and
(C) activating a contamination control device in accordance with the processing of the image data,
wherein the image data is processed using a stabilization algorithm to determine whether the image data satisfies a threshold image value for a threshold time period, with the threshold image value being a pre-determined minimum image value correlating with an absence of the contamination event or a pre-determined minimum image value correlating with a presence of the contamination event, and the threshold time period being a pre-determined minimum time period that the threshold image value is satisfied.

2. The automated process according to claim 1, wherein the contamination event is a germ-releasing event or a germ-spreading event.

3. The automated process according to claim 1, wherein the image data is captured by scanning at least a portion of the production area with a camera.

4. The automated process according to claim 1, wherein at least one member selected from the production area, the individual, and the contamination control equipment has an RFID tag thereon.

5. The automated process according to claim 1, wherein activating the contamination control device comprises at least one member selected from the group consisting of: (i) cutting off power to at least one machine in the production area, and (ii) interjecting a physical restraint or barrier between the individual and at least a portion of the production area, and (iii) sounding an alarm comprising at least one member selected from the group consisting of an audible alarm, a visual alarm, and a vibratory alarm, and (iv) generating and transmitting a report, with the transmission of the report comprising at least one member selected from the group consisting of transmission of an electronic report and transmission of a hard copy report.

6. The automated process for monitoring and controlling contamination activity in a production area according to claim 1, wherein the contamination event comprises at least one member selected from the group consisting of coughing, sneezing, sweating, spitting, bleeding, vomiting, belching, crying, excreting, spilling, breaking, dropping, touching, breathing on, a leaking pipe, a breaking pipe, a light bulb exploding, and a production equipment breaking and releasing parts or fragments.

7. The automated process for monitoring and controlling contamination activity in a production area according to claim 1, wherein the contamination event comprises an action outside the production area that cause the release of a contaminant into or within the production area, comprising at least one member selected from the group consisting of fire releasing particulates into the environment of the production area, vibration absorbed by the production area releasing particulates from a surface within the production area, a lightning strike into or near the production area causing a contaminate to be released into the production area, wind causing release of particulates from surfaces outside the production area into the production area.

8. An automated process for monitoring and controlling contamination activity in a production area, comprising:
(A) capturing image data from the production area over a period of time;
(B) processing the image data with a computer to determine whether a contamination event has occurred in the production area, wherein the processing of the image data further comprises processing the image data with a computer to determine:
  (i) whether an individual is present within the production area,
  (ii) whether the individual has engaged in the contamination event while in the production area,
  (iii) whether an article of contamination control equipment is present in association with the individual during the contamination event, and
  (iv) whether the article of contamination control equipment is properly positioned or properly configured during the contamination event; and
(C) activating a contamination control device in accordance with the processing of the image data,
wherein the image data is processed to find an image of at least a portion of the individual present in the production area while the individual is in motion, with the image data being processed using a stabilization algorithm to determine whether the image data satisfies a threshold image value for a threshold time period, with the threshold image value being a pre-determined minimum image value correlating with an absence of the contamination event by the individual and/or a pre-determined minimum image value correlating with the contamination control equipment being present and properly positioned while the individual is in the production area, with the threshold time period being a pre-determined minimum time period that the threshold image value is satisfied, and the activation of the contamination control device providing a positive indication of an absence of the contamination event by the individual.

9. An automated process for monitoring and controlling contamination activity in a production area, comprising:
(A) capturing image data from the production area over a period of time;
(B) processing the image data with a computer to determine whether a contamination event has occurred in the production area, wherein the processing of the image data further comprises processing the image data with a computer to determine:
  (i) whether an individual is present within the production area,
  (ii) whether the individual has engaged in the contamination event while in the production area,
  (iii) whether an article of contamination control equipment is present in association with the individual during the contamination event, and
  (iv) whether the article of contamination control equipment is properly positioned or properly configured during the contamination event; and
(C) activating a contamination control device in accordance with the processing of the image data,
wherein the image data is processed to find an image of at least a portion of the individual present in the production area while the individual is in motion, with the image data being processed using a stabilization algorithm to determine whether the image data satisfies a threshold image value for a threshold time period, with the threshold image value being a pre-determined minimum image value correlating with the occurrence of the contamination event by the individual and a pre-determined minimum image value correlating with the contamination control equipment being absent or improperly positioned during the contamination event, with the threshold time period being a pre-determined minimum time period that the threshold image value is satisfied, and the contamination control device being activated to provide a positive indication of the contamination event in the production area, due to a determination of both:
  (i) the occurrence of the contamination event in the production area, and
  (ii) the absence or improper positioning of the contamination control equipment during the contamination event.

10. The automated process according to claim 9, wherein the contamination event is a germ-releasing event and the contamination control equipment comprises at least one member selected from the group consisting of a glove, a face mask, a suit, a gown, and a hair net, and a product article comprising food.

11. The automated process according to claim 9, wherein the process further comprises:
   processing the image data to determine the location in the production area of the individual when the contamination event occurs; and
   processing the image data to identify at least one potentially contaminated product article and/or identify at least one potentially contaminated production article that is within a contamination zone produced by the contamination event.

12. The automated process according to claim 11, wherein the contamination control device comprises an automated report generator that processes the image data to generate a report including an identity of the at least one potentially contaminated product article and/or the at least one potentially contaminated production article within the contamination zone at the time of occurrence of the contamination event.

13. The automated process according to claim 11, wherein the potentially contaminated product article and/or potentially contaminated production article within the contamination zone is in motion during and/or after the contamination event, with the automated process further comprising processing the image data to track the location of the at least one potentially contaminated product article and/or potentially contaminated production article after the contamination event, so that identity and location of the potentially contaminated product article in the contamination zone and/or potentially contaminated production article in the contamination zone is known after the contamination event, with the tracking of the at least one potentially contaminated product article and/or potentially contaminated production article being carried out using the stabilization algorithm to determine whether the image data satisfies a threshold image value for a threshold time period, with the threshold image value being a pre-determined minimum image value correlating with the identity of the at least one potentially contaminated product article and/or the at least one potentially contaminated production article, and the threshold time period being a pre-determined minimum time period that the threshold image value is satisfied.

14. The automated process according to claim 9, wherein the activating of the contamination control device comprises activating at least one member selected from group consisting of:
   (i) an alarm to notify the individual that the article of contamination control equipment is not present or is not properly positioned;
   (ii) an automated report generator that processes the image data to generate a report including information pertaining to the article of contamination control equipment not being present or not being properly positioned during the contamination event; and
   (iii) equipment to decontaminate, move, reposition, shield, or discard the at least one potentially contaminated product article and/or the at least one potentially contaminated production article within the contamination zone at the time of the contamination event.

15. The automated process according to claim 14, wherein the automated report generator processes the image data to generate a report that includes an image of the individual in the production area while the threshold image value is satisfied for the threshold time period, and a notation of a time at which the image was captured.

16. An automated system for monitoring and controlling contamination in a production area, the system comprising:
   (A) a computer;
   (B) an image sensor in communication with the computer, the image sensor being configured and arranged to capture image data of at least a portion of the production area; and
   (C) computer-readable program code disposed on the computer, the computer-readable program code comprising:
      (i) a first executable portion for processing the image data to produce an image of at least the portion of the production area captured by the image sensor,
      (ii) a second executable portion for processing image data and determining if a contamination event occurs within the portion of the production area captured by the image sensor,
      (iii) a third executable portion for activating a contamination control device in accordance with the processing of the image data, and
      (iv) a stabilization algorithm to determine whether the image data satisfies a threshold image value for a threshold time period, with the threshold image value being a pre-determined minimum image value correlating with an absence of the contamination event or a pre-determined minimum image value correlating with a presence of the contamination event, and the threshold time period being a pre-determined minimum time period that the threshold image value is satisfied.

17. The automated system according to claim 16, wherein the computer-readable program code further comprises an executable portion for processing the image data and determining whether an article of contamination control equipment is present and properly positioned or properly configured in the image data captured by the image sensor.

18. The automated system according to claim 16, wherein the computer-readable program code further comprises an executable portion for processing the image data to find an image of an individual in the image data captured by the image sensor.

19. The automated system according to claim 18, wherein the computer-readable program code comprises an executable portion for determining whether the individual has engaged in the contamination event while in the production area.

20. The automated system according to claim 19, wherein the computer-readable program code further comprises an executable portion for processing the image data and determining whether an article of contamination control equipment is present and properly positioned on the individual in the production area.

21. The automated system according to claim 16, wherein the computer-readable program code further comprises an executable portion for processing the image data to identify at least one potentially contaminated product article and/or identify at least one potentially product article that is within a contamination zone produced by the contamination event.

22. The automated system according to claim 21, wherein the computer-readable program code further comprises an executable portion for tracking the at least one potentially contaminated product article that is within the contamination zone produced by the contamination event.

23. The automated system according to claim 21, wherein the computer-readable program code further comprises an executable portion for marking the at least one potentially contaminated product article that is within the contamination zone produced by the contamination event.

24. The automated system according to claim 16, wherein the image sensor is a first image sensor in communication with the computer and the system further comprises a second image sensor in communication with the computer, and the first image sensor capturing image data from a first portion of the production area and the second image sensor capturing image data from a second portion of the production area, with both the first and second image sensors being in communication with the computer, with the computer-readable program code processing image data from both the first image sensor and the second image sensor.

25. The automated system according to claim 16, wherein the image sensor is a scanning imaging sensor configured and arranged to scan the production area.

26. The automated system according to claim 16, further comprising a data entry device in communication with the computer.

27. The automated system according to claim 16, further comprising a printer in communication with the computer, the printer being capable of printing a report of a determination of whether the contamination event has or has not occurred.

28. The automated system according to claim 16, wherein the computer-readable program code further comprises an executable portion for processing the image data to find an image of an individual in the image data captured by the image sensor, and an executable portion for determining whether the individual has engaged in the contamination event while in the production area, and an executable portion for determining whether contamination control equipment is properly positioned on the individual in the production area, and an executable portion for processing the image data to identify at least one potentially contaminated product article within a contamination zone produced by the contamination event, and wherein the computer-readable program code further comprises a stabilization algorithm to determine whether the image data satisfies a threshold image value for a threshold time period, with the threshold image value being a pre-determined minimum image value correlating with a presence of the contamination event, and the threshold time period being a pre-determined minimum time period that the threshold image value is satisfied.

\* \* \* \* \*